United States Patent [19]

Guerrero

[11] Patent Number: 5,176,645
[45] Date of Patent: Jan. 5, 1993

[54] PNEUMATIC, MODULAR DEVICE FOR DISPENSING MEDICATION TO ANIMALS

[75] Inventor: Fernando Guerrero, West Chester, Pa.

[73] Assignee: Diana Corporation, West Chester, Pa.

[21] Appl. No.: 694,089

[22] Filed: May 1, 1991

[51] Int. Cl.$^5$ .............................................. A61M 5/20
[52] U.S. Cl. ..................................... 604/143; 604/150
[58] Field of Search ................. 604/70, 140, 141, 143, 604/146, 147, 150

[56] References Cited

U.S. PATENT DOCUMENTS

| | | | |
|---|---|---|---|
| 3,189,029 | 6/1965 | Stephens | 604/70 |
| 3,353,537 | 11/1967 | Knox | 604/143 |
| 3,481,323 | 12/1969 | Cook et al. | 604/143 |
| 3,515,130 | 6/1970 | Tsujino | 604/147 |
| 3,784,063 | 1/1974 | Otis et al. | 604/141 |
| 3,859,996 | 1/1975 | Mizzy et al. | 604/70 |
| 4,426,024 | 1/1984 | Hogan et al. | 604/141 |
| 4,561,856 | 12/1985 | Cochran | 604/143 |
| 4,601,709 | 7/1986 | Kabbaby | 604/150 |
| 4,744,786 | 5/1988 | Hooven | 604/143 |
| 4,790,824 | 12/1988 | Morrow | 604/143 |
| 5,009,637 | 4/1991 | Newman et al. | 604/143 |
| 5,015,237 | 5/1991 | Kleinwolterink, Jr. et al. | 604/143 |

Primary Examiner—Paul J. Hirsch

[57] ABSTRACT

A pneumatic powered, modular device, suitable for giving an adjustable dose of liquid medication to animals drawing the liquid from a bulk container. Modular design permits several ranges of dosage as well as methods of delivery such as hypodermic, oral or poured on skin. In FIG. 1 we show the hypodermic mode. Compressed air enters handle 1 at base through fitting 18, goes through passage 19 into 3 way valve 21 normally closed. Depressing trigger 22 allows air to enter chamber 24 pushing piston 7 forward. Liquid in front of piston 7 is expelled past check valve 25 into chamber 26 and out of hypodermic needle. Gasket 30 holds liquid in. For oral delivery, terminal 35 is substituted. Upon release of trigger 22, 3 way valve 21 permits air on chamber 24 to exhaust via exit 31 on valve, spring 11 pulls piston back until fitting expansion 13 stops against adjustable nut 6. This determines size of dosage. Liquid is suctioned from bulk tank not shown via tube 15 through check ball 16 and into front of piston chamber 7.

5 Claims, 4 Drawing Sheets

PNEUMATIC, MODULAR DEVICE FOR DISPENSING MEDICATION TO ANIMALS

BACKGROUND OF THE INVENTION

A. Field of Invention

The present invention relates to a pneumatic gun or device which can be adapted to medicate animals in different ways and in different ranges, said gun is for use in mass production settings such as a feed lot processing station.

In feed lots it is common to direct cattle to a work station where they are immobilized. At this point the animal is tagged, dehorned, vaccinated, given injections, given oral dewormers, castrated, and given insect protection poured on its skin (known as "pour on"). This pour on is commonly done using a hand held measuring cup which exposes the worker to toxic chemicals. All these operations are performed by a crew of workers at the rate of as much as 5,000 cattle or more in an eight hour shift.

There is a need for low cost equipment to ease the work load and minimize the exposure of workers to toxic chemicals. Our equipment is modular in design and made of plastic parts thus lowering the cost of manufacture, and it is powered by compressed air thus greatly reducing the effect of delivery of medication for the operator. The medication travels though a closed system from the container to the animal thus decreasing operator exposure to toxic chemicals.

B. Description of Prior Art

Commonly used equipment is hand powered. Typical squeeze type guns are made by Phillips Company of Australia (U.S. Pat. No. 182,110) or Instrument Supplies Co. of New Zealand (NZ Pat. 222692). They include a 2 piece handle which is squeezed to push liquid in syringe out through a hypodermic or oral tube. These hand operated guns tend to cause operator fatigue when used over extended periods. Our company (Diana corporation) has manufactured a non-modular medicating device which is air powered and which has been successful in reducing worker fatigue. The success of this first powered device prompted the development of a low cost plastic molded gun that would be modular so that one set of plastic molds could be used to produce many permutations and thus create an affordable powered doser.

Applicant submits that none of prior patents cover simultaneously the features of 1) a closed system with repeatable dose from a separate tank; 2) adjustable dose; and 3) modular construction.

- Kleinwolternick (U.S. Pat. No. 5,015,327) is not a repeater device. It is only a remote hypodermic device. It must have its liquid medication recharged each time. It has no provision for dose adjustment.
- Tsujino (U.S. Pat. No. 3,515,130) does not have an adjustable dosage feature, is not contemplated as an oral doser, is not pneumatic powered, nor does it show features making it a low cost modular device.
- Stephens (U.S. Pat. No. 3,189,029) is a single shot applicator and is not adjustable in dosage.
- Kabbaby (U.S. Pat. No. 4,601,709) is a proportioning device for medication into a larger fluid stream, it is not a multiple doser with adjustable delivery.
- Cochrin (U.S. Pat. No. 4,561,856) is not a repeater device. Its use is for controllable slow delivery rate.
- Knox (U.S. Pat. No. 3,353,537) is similar to our application but it is a much more complicated construction. They have a separate chamber for compressed gas (27) and two separate pistons for gas and liquid (57 and 60). The design does not contemplate low cost modular manufacturing for multiple use. The adjustment of the dose is a complicated method needing an indicator (97, 95, 94). Such a device can become inaccurate after some use and is inherently dangerous because of possible overdose of medication. The liquid inlet location is an obstacle to ease of handling as opposed to our design with rear inlet.

SUMMARY

The present invention is an air powered medication doser gun which is modular in design and built of plastic molded parts in such a way that the same gun can be converted for many uses making it possible to produce in more economic quantities. By exchanging barrels and pistons it can deliver 30 ml, 10 ml, 2 ml or 200 ml all adjustable from 0 ml to maximum. Gun may use a hypodermic needle, an oral tube, or a skin "pour on" tube with shower head. It is planned to adapt a high pressure needleless hypodermic attachment although this is still under development.

Advantages of this design is that simultaneously 1) it is air powered and thus reduces the fatigue of the operator; 2) it is modular thus reducing cost by allowing larger productions runs thereby making it practical to injection mold; and 3) it offers a closed system thus minimizing the risk of operator exposure to toxic chemicals.

BRIEF DESCRIPTION OF DRAWINGS

FIG. 1a shows a cross section of an adaptor for the luer fitting depicted in FIG. 1.

DESCRIPTION OF PREFERRED EMBODIMENT

Figure 1:
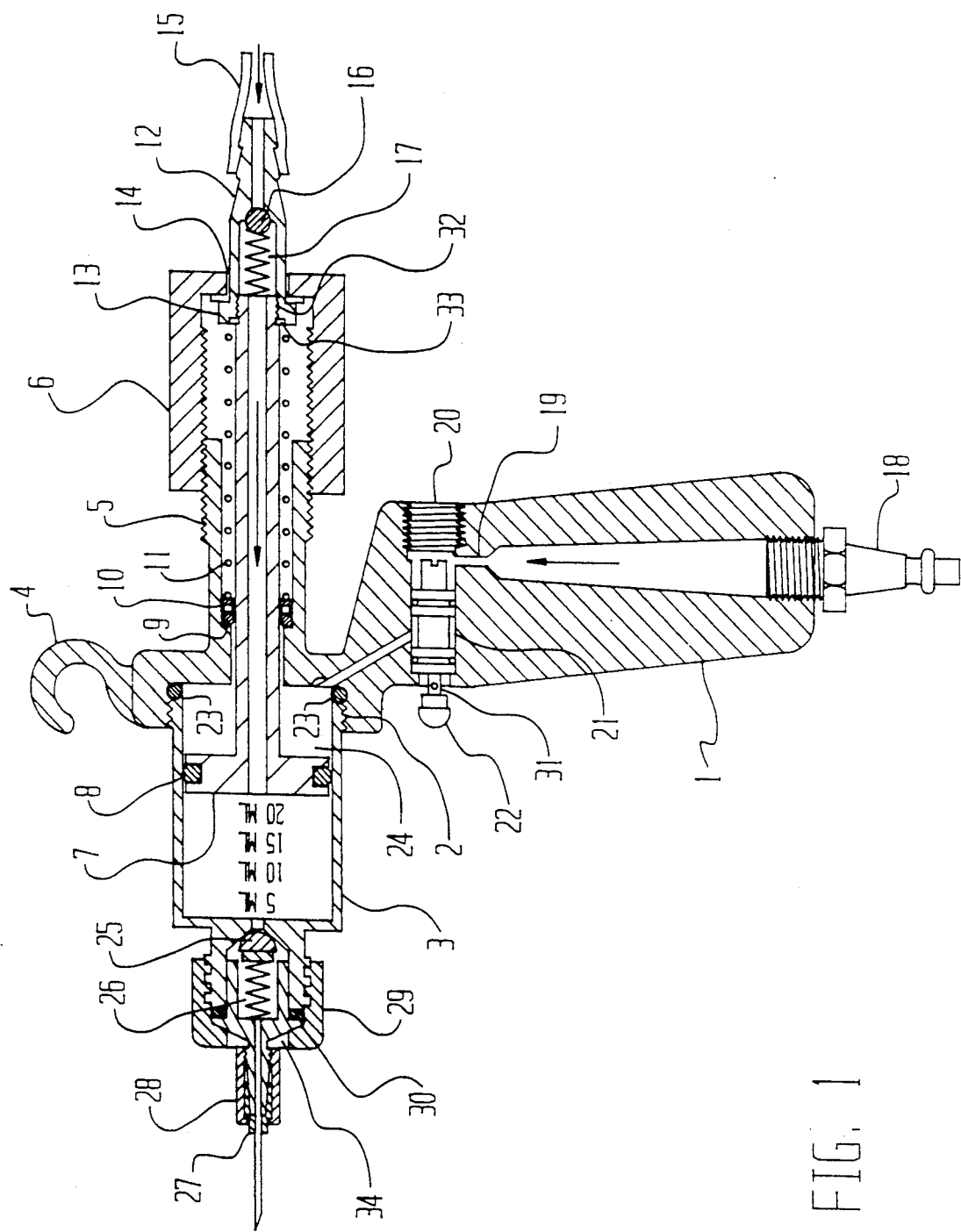
FIG. 1 shows a cross section of modular gun.

FIG. 1 is a sectional view of the modular unit, configured as a hypodermic injector. The unit consists of a plastic molded main body, with handle 1, female thread 2, that engages with barrel 3, which has corresponding male threads. The main body has an integral hook 4 for holding the unit when not in use. A male thread 5 on the main body engages with female thread on the stroke-adjustment-nut 6. The piston and rod 7, contains sealing ring 8 within its flanges, which slides against cylinder 3. The air chamber 24 is sealed by rod O-ring 9 and U-cup 10 which are contained by the main spring 11. The particular combination of an O-ring and U-cup can be changed to a variety of sealing methods. A male thread 32 on rod 7 engages with a female tread on inlet fitting 12. O-ring 33 seals this connection. Inlet fitting 12 slides freely in hole 14 at the end of the stroke adjusting nut 6, however the large diameter section 13 will not pass, thus limiting the backward travel of piston and rod 7.

This travel is caused by compression spring 11 pushing between U-cup 10 and the end of inlet fitting 12. By rotating stoke adjusting nut 6, the backward travel limit of piston and rod 7 is adjusted, and thus the shot volume is adjusted. Cylinder 3, which is translucent, is calibrated in milliliters (or any scale). Visibility aligning the front piston and rod 7 with these calibrations will give the desired shot volume.

Inlet fitting 12 has a serrated end to which a flexible hose is attached. This hose goes to a liquid supply bottle (not shown) and conveys liquid into the system. Check ball 16, held in place by spring 17, allows liquid in on backstroke of piston, but not out on forward stroke. Incoming liquid travels through the hollow rod 7 into cylinder in front to piston during the backstroke.

Compressed gas at suitable pressure (approx. 80 p.s.i.) enters bottom of main body via a male quick-disconnect fitting 18. Gas passes through hole 19 into chamber behind normally-closed three-way valve 21. Plug 20 keeps chamber pressurized. Depressing trigger 22 actuates valve 21 and allows gas into chamber 24 behind piston. Gas in chamber 24 is contained by seal 23 and sliding seals 8, 9, and 10. Gas will push piston forward completely. Movement of piston forces liquid past check valve 25, held by spring 26, and into hypodermic needle.

Releasing trigger 22 allows air to exhaust via hole 31 on valve stem, permitting main spring 11 to pull piston back.

In this unit luer adaptor 34 is shown holding hypodermic needle 27 with a cap 28 to lock needle. Plastic cap 29 and seal 30 holds the assembly together and liquid tight.

Figure 2:
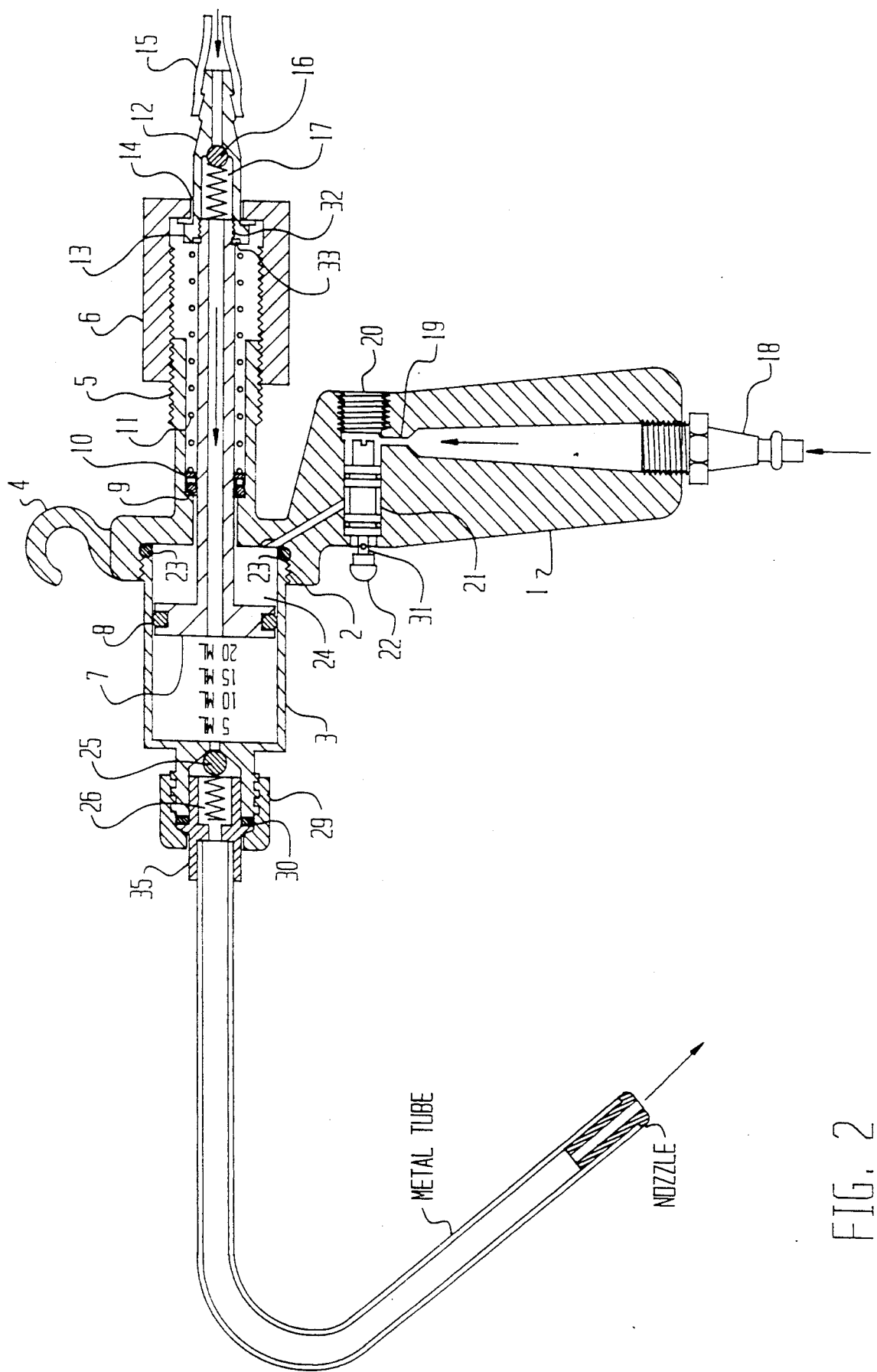
FIG. 2 shows identical view of gun with oral dosing tube.
Figure 3:
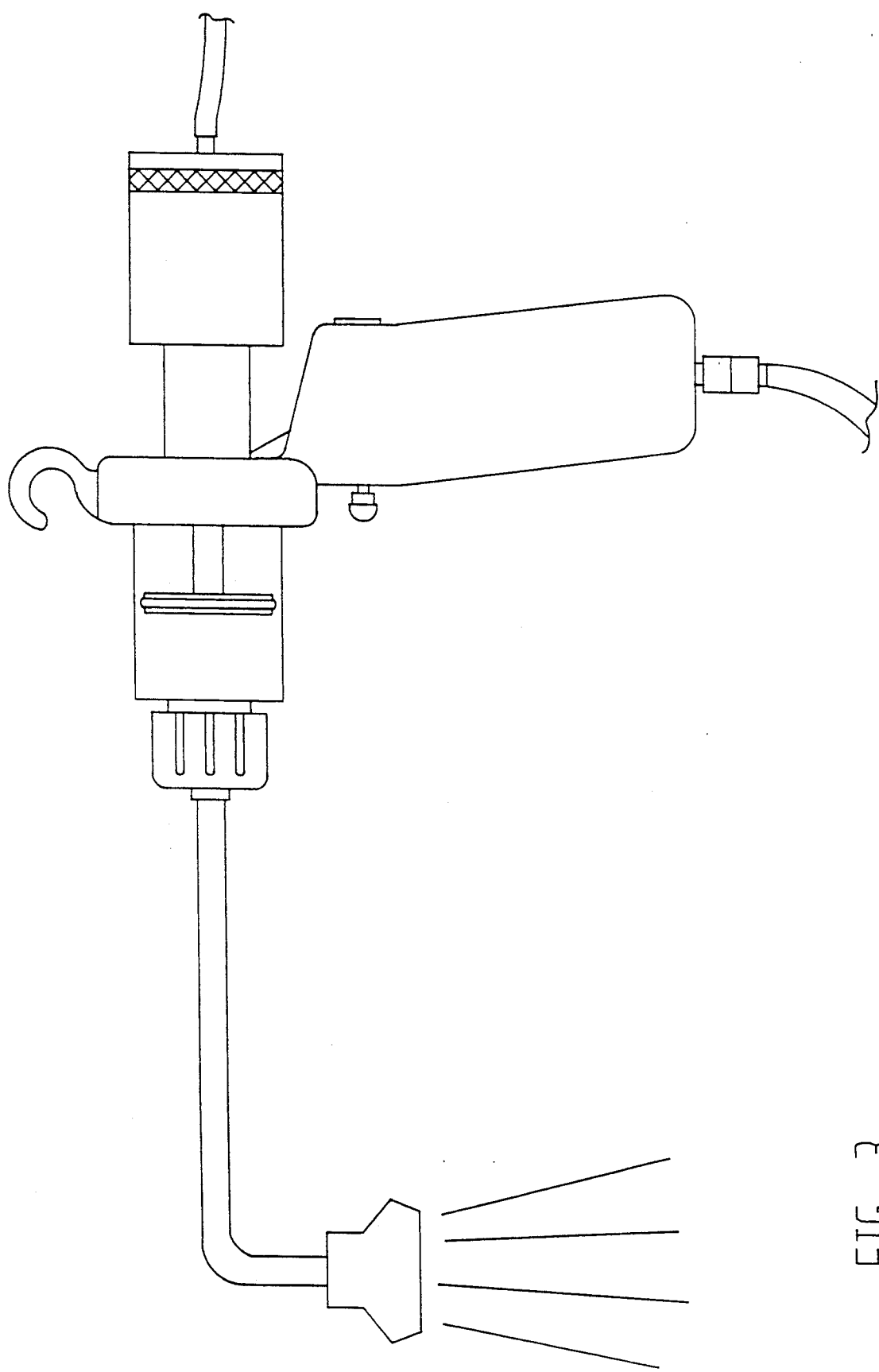
FIG. 3 shows outside view of gun with a skin dosing tube and shower head.
Figure 4:
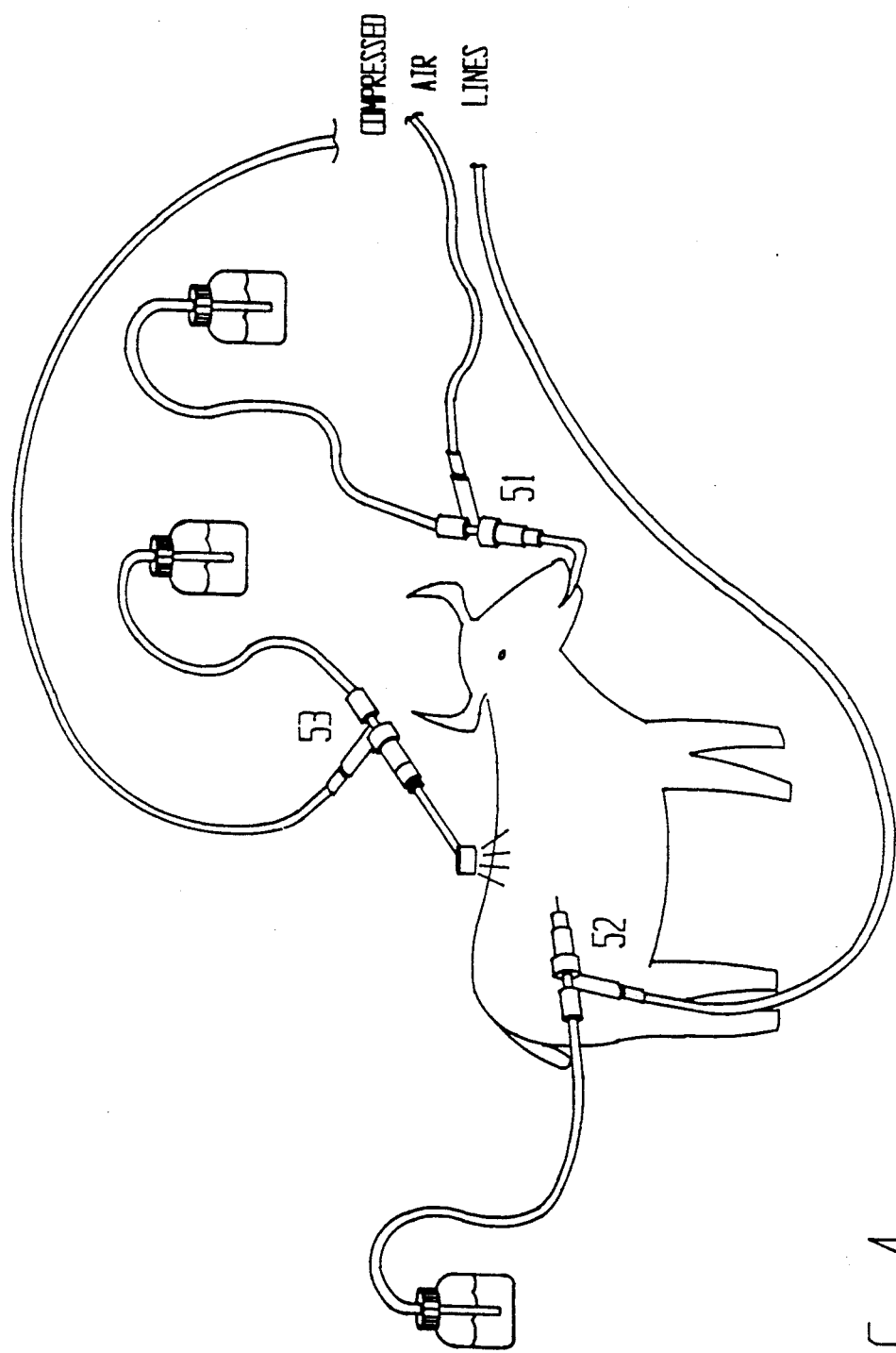
FIG. 4 shows general work stations where gun 51 is giving an oral medication, gun 52 is giving a hypodermic medication and gun 53 is giving an external dose.

In FIG. 2, instead of a luer adaptor, a ⅜ inch diameter tube with adapter 35 can be used, bent to dose liquid orally. Likewise, a straight tube with a shower head can be used to dispense liquid onto an animal's back, as in FIG. 3. In these two cases, the tube is mounted to the cylinder by means of adapter 35.

What is claimed is:

1. A modular gun assembly for delivering an adjustable measured dose of medication comprising:
   a handle portion including a handle means, means for attaching a piston assembly at a forward face of said handle portion, said piston assembly including a container, a piston having an adjustable stroke length within said container, a means for delivering said dose from said container to an animal and means at a rearward face of said handle portion to attach a means for adjusting said dose, said means for adjusting comprising means to selectively limit the rearward movement of said piston within said container,
   means for supplying said medication through said adjusting means and said piston to said container forward of a front face of said piston,
   valve means connected to said handle portion for selectively driving said piston,
   means within said handle means and connected by a conduit to the rear face of said piston for delivering a source of compressed gas or fluid for driving said piston, whereby actuation of said valve means ejects said medication.

2. A modular gun assembly according to claim 1, wherein said means for delivering said dose is a needle.

3. A modular gun assembly according to claim 1, wherein said means for delivering said dose is a shower head.

4. A modular gun assembly according to claim 1, wherein said means for delivering said dose is a tube for orally dispensing of said medication.

5. A modular gun assembly according to claim 1, wherein said container is translucent and includes indicia for indicating the dose of medication within said container.

* * * * *